United States Patent [19]
Gray

[11] Patent Number: 5,269,081
[45] Date of Patent: Dec. 14, 1993

[54] FORCE MONITORING SHOE

[76] Inventor: Frank B. Gray, 5104 Lyons View Pike, Knoxville, Tenn. 37919

[21] Appl. No.: 877,230

[22] Filed: May 1, 1992

[51] Int. Cl.⁵ .............................................. A61B 5/11
[52] U.S. Cl. ...................... 36/136; 36/139; 128/779; 73/172
[58] Field of Search ............... 36/136, 132, 137, 139; 128/779, 25 B; 73/172; 340/573

[56] References Cited

U.S. PATENT DOCUMENTS

| | | | |
|---|---|---|---|
| 1,933,243 | 10/1933 | Merolis et al. | 36/137 X |
| 3,702,999 | 11/1972 | Gradisar | 36/139 X |
| 3,731,674 | 5/1973 | Parvin | 36/136 X |
| 3,791,375 | 2/1974 | Pfeiffer | 36/139 X |
| 3,974,491 | 8/1976 | Sipe | 36/137 X |
| 4,426,884 | 1/1984 | Polchaninoff | 73/172 |
| 4,503,705 | 3/1985 | Polchaninoff | 73/172 |
| 4,647,918 | 3/1987 | Goforth | 340/573 |
| 4,745,930 | 5/1988 | Confer | 128/779 |
| 4,814,661 | 3/1989 | Ratzlaff et al. | 36/136 X |
| 4,918,851 | 4/1990 | Peikin | 36/4 |
| 5,042,504 | 8/1991 | Huberti | 128/779 |
| 5,107,854 | 4/1992 | Knotts et al. | 128/779 |
| 5,113,850 | 5/1992 | Larremore et al. | 128/32 |

FOREIGN PATENT DOCUMENTS

| | | | |
|---|---|---|---|
| 3743835 | 4/1989 | Fed. Rep. of Germany | 128/779 |
| 8203753 | 11/1982 | World Int. Prop. O. | 36/136 |

OTHER PUBLICATIONS

Novel electronics inc., "mini emed system", pp. 1-2.

*Primary Examiner*—Steven N. Meyers
*Assistant Examiner*—Ted Kavanaugh
*Attorney, Agent, or Firm*—Pitts & Brittian

[57] ABSTRACT

A force monitoring shoe (10) for monitoring the force being applied to a patient's leg, as during walking. The device is contained within a shoe-like enclosure which can be worn by a recuperating injured person. Provision is made, as with a spring, to absorb the shock of the step. When force equal to a selectable value has been applied, an alert system notifies the patient. With this device a recovering patient will know exactly how much weight to place on the leg during every step.

16 Claims, 3 Drawing Sheets

FORCE MONITORING SHOE

TECHNICAL FIELD

This device relates generally to force monitoring systems and, in particular, to systems which measure the force applied to a person's leg during standing, walking, and similar activities. A force sensitive device absorbs the force from the foot, which is then compared to a pre-selected amount of force. When the proper amount of force has been applied to the shoe, a signalling device alerts the patient, such that excessive weight will not be applied.

BACKGROUND ART

During rehabilitation, patients are often asked by their physicians to apply a specific amount of weight on a body part, for example, during recuperation following a full knee replacement. While total isolation of the leg may be unnecessary, the leg may not be strong enough to support the full body weight of the person. As a result, the doctor will typically instruct the patient to apply 40%, for example, of his full weight upon the leg. This scenario is also common among other medical treatments such as hip replacements, healing of broken bones, pulled muscles, etc. In some cases, applied pressure is required for proper healing, for example, medical testing has shown that broken bones heal best along stress lines. Thus, the application of pressure to an injured limb often enhances its recovery.

The amount of force applied to the injured limb is significant because too much force can aggravate injuries, but too little force will not promote healing. For example, if a person is recuperating from a pulled muscle, some force is desired, but if the muscle is not fully recovered, too much pressure can cause re-injury of the muscle. Conversely, if a broken bone is to heal properly, force must be applied to the limb. If too little force is applied, fusion of the bone fragments will not occur and proper healing will take longer than necessary. The patient must apply enough force to aid the healing process, while taking precautions to prevent further damage.

The problem arises in that patients can not always accurately determine how much weight they are applying to their leg. Common practice has been to have the patient stand on a scale and place, for example, 30 pounds on the leg to see how it feels. The patient is then asked to reproduce that feeling with every step, a practically impossible task. A system is required that can sense the amount of weight being applied and then inform the patient when the proper level has been reached.

Prior systems have been developed that study pressure exerted by the foot. Most notably, a system called "Emed" was developed by Novel Electronics Inc. of Minneapolis, Minn. This system requires the patient to walk across an electronic pad, which is able to sense the pressure applied at various points and convey that information to a computer. Emed is usually operated by a medical practitioner in a doctor's office, where it provides complex and detailed stress analysis data. Emed can not be operated by the patient and returns data from one step. It is not portable and can not be used during daily walking. A system for promoting the healing of the aforementioned injuries should be able to convey directly to the patient, information regarding the amount of weight being supported by a limb during every step.

Accordingly, it is an object of the present invention to provide a device that will sense the amount of force being applied upon a leg by every step taken.

It is a further object of the invention to provide a device that will convey a signal to the operator when the desired amount of force has been applied to the leg.

It is another object of the present invention to provide a device that will produce an output signal whenever a pre-selected force has been applied such that this output signal can be recorded for future analysis thereof.

These and other objects of the present invention will become apparent upon the consideration of the following description with reference to the drawings referred to therein.

DISCLOSURE OF THE INVENTION

According to the present invention there is provided a shoe-like enclosure, referred to hereinafter as shoe, with cavities containing a force absorption scheme, a force monitoring device, and a signalling system. The force absorption device within the shoe comprises a system for accepting the shock placed upon the shoe using, for example, springs, hydraulics, or any other suitable means. The force monitoring apparatus then compares the applied force with a desired, pre-selected amount of force. The alert system will notify the shoe wearer when the correct amount of force has been applied. In one embodiment, the shoe can be worn daily as if it were a normal shoe or, other considerations are provided in an embodiment implemented for people with casts.

BRIEF DESCRIPTION OF THE DRAWINGS

The above mentioned features of the invention will become more clearly understood from the following detailed description of the invention read together with the drawings in which.

BEST MODE FOR CARRYING OUT THE INVENTION

Figure 1:
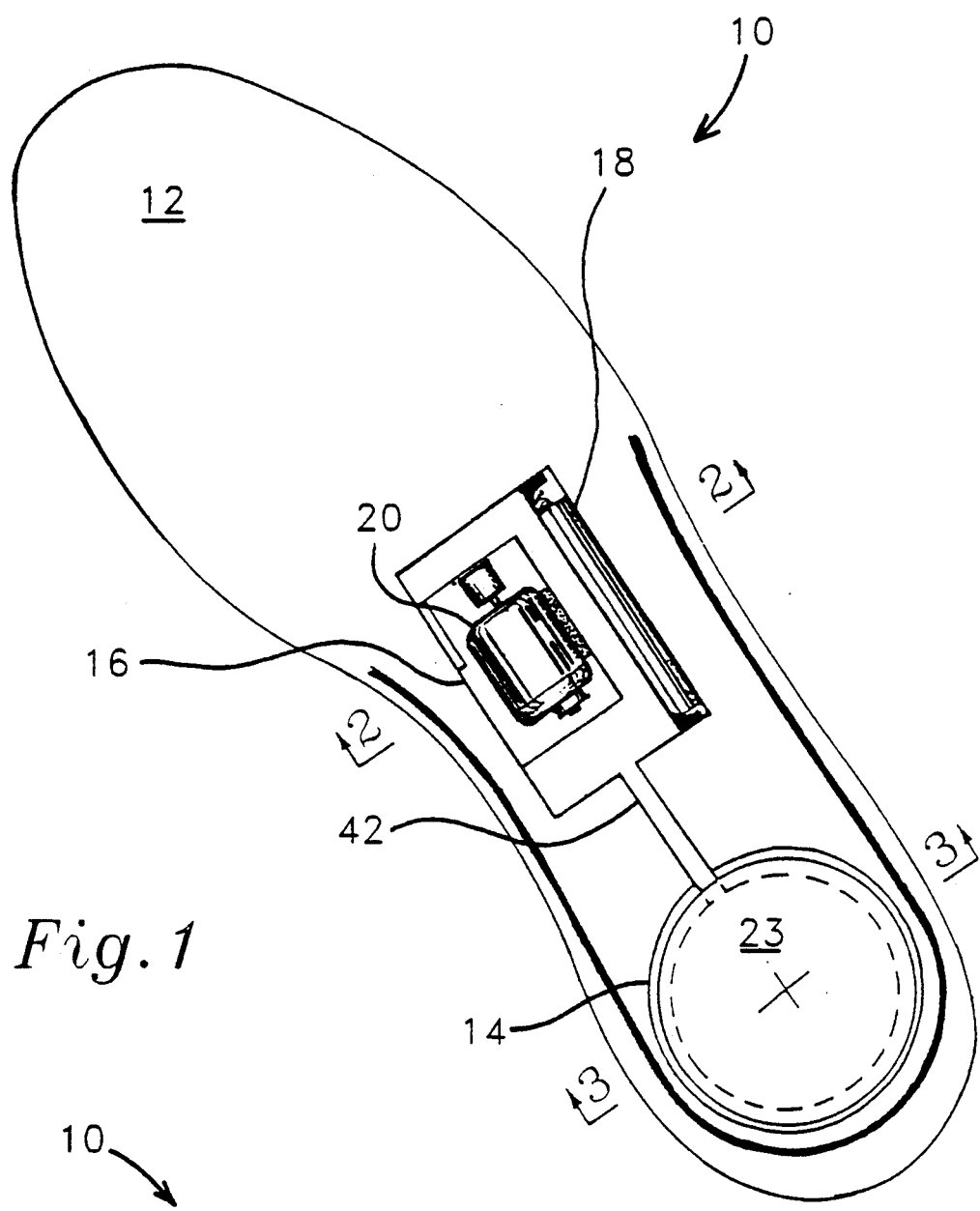
FIG. 1 is a drawing, partially cut away, illustrating the sole of a shoe-like device according to the present invention.

Shown generally at 10 in FIG. 1 is the force monitoring shoe of the present invention. The force monitoring shoe 10 is intended to aid in the recovery of patients with insults to the lower extremity and pelvis, such as post-operative states, fractures, and some soft tissue injuries, etc. During the recuperation period, the amount of force applied to the leg is often critical. Inadequate force can hinder the healing process, while undue force can cause additional injuries. This device 10 will monitor the amount of force applied to the leg during every step and give the patient a signal when a pre-selected amount of force has been applied. The amount of force desired is generally the optimal force for promoting healing of the limb at that given point in time, taking into consideration the type of injury and how close to full recovery the patient has come.

In the preferred embodiment, cavities 14, 16, and 42 are necessary for enclosing the components of the force monitoring shoe 10, as illustrated in FIG. 1. Cavity 14 can hold devices for absorbing the force applied by the patient's foot and comparing it with a pre-selected desired value, while cavity 16 can encapsulate all or part of the components required for signalling the patient when the pre-selected value has been attained. A tunnel-like cavity 42 is provided such that connections, such as electric wires and pressure hoses can be made between the components of cavity 14 and cavity 16. While cavity 14 has been shown located at the heel of the shoe sole 12 in FIG. 1, it will be known that cavity 14 and any components contained within can be placed anywhere in the shoe sole 12. In the preferred embodiment, cavity 16 encloses a power means 18, a patient signalling means, in this case a vibrational motor 20 and any connections, such as electrical wires 46 (see FIG. 3), required between the two. Cavity 16 can also be placed anywhere in the shoe 12 without a loss of function and may, alternatively, contain the power means 18, with the signalling device being located elsewhere inside or adjacent to the shoe 10.

Figure 2:
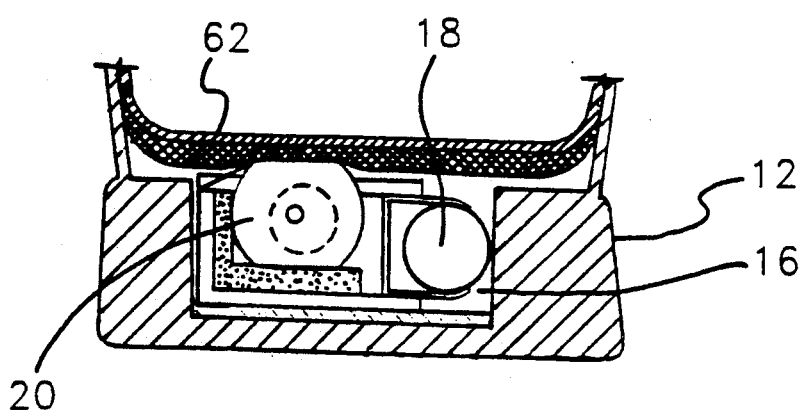
FIG. 2 is a cross sectional view of the shoe sole of FIG. 1 taken at 2—2, thereof illustrating a power source for the present invention and vibratory signalling means to indicate to a wearer of the shoe that the pre-selected force has been achieved or exceeded.

Shown in FIG. 2 is a cross section taken along 2—2 of FIG. 1. In the preferred embodiment, cavity 16 contains a power means 18, such as a battery, and a signalling device. Since a vibrational means 20 is employed as the signalling device in this embodiment, the upper portion of the cavity is noticeably raised as compared to the remainder of the insole of the force monitoring shoe 10. This height difference is designed such that the covering 62 of cavity 16 will come in contact with the foot of the patient. It will be understood that the covering 62 may be the removable liner typically provided in the shoe 10, and may further serve to cover cavities 14,42. The liner provides comfort for the wearer and further protects the user's foot from edema due to the cavity 16. As will be seen below, the liner also retains a platform 23 in a selected position, the platform 23 being provided to concentrate the load applied to the shoe 10 by the user. Contact between the foot of the patient and the vibrational means 20 will ensure that the patient feels the signal. If a signalling means other the vibrational means 20 is employed, heightening the cover 62 of cavity 18 may not be necessary.

Figure 3:
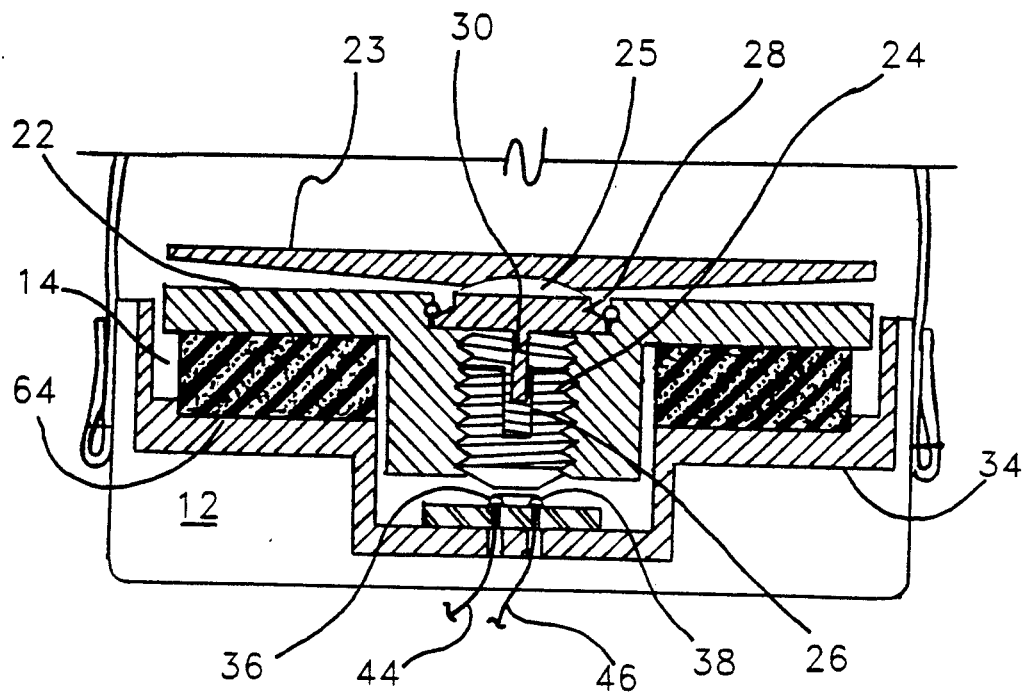
FIG. 3 is a cross-sectional view of the shoe sole of FIG. 1 taken at 3—3, thereof illustrating one embodiment of means for determining the occurrence of a pre-selected force applied to the shoe sole.

Illustrated in FIG. 3 is a cross section taken along line 3—3 of FIG. 1. FIG. 3 pictures one of the possible embodiments for the components contained in cavity 14 for absorbing the applied force and comparing it with the pre-selected desired force. This embodiment comprises a piston 22, exposed to force exerted by the foot of the patient through a platform 23 and a dial 28, and whose bottom is connected to a force absorption system 64, a resilient material such as rubber, in this embodiment. As can be seen from the figures, force applied to the platform 23 is transferred through the central portion of the platform 23 to the dial 28 and subsequently to the piston 22. For stability, the bottom of the force absorption means 64 is then connected to a base 34, which is attached to the sole of the shoe 10. Located in the center of the piston 22 is an adjustable screw 24, whose bottom end is electrically conductive. A dial 28 with an adjustment notch 25 is provided to rotate the adjustable screw 24 by means of a tang 30 on dial 28 engaging slot 26 in adjustable screw 24, thus moving it vertically relative to the piston. Placed directly below the electrically conductive end of screw 24 are two electrical contacts 36,38. The contacts 36,38 are attached to the base 34 and further attached to electrical wires 44,46. These wires 44,46 can be connected in a circuit to the patient signalling means described earlier, or connected to an external processing system (not shown). When the two contacts become electrically connected, the circuit will be energized, thus the patient signalling means will be activated.

The embodiment in FIG. 3 employs the various components to absorb the force applied by the foot of the patient, and compare it with an adjustable value. The patient applies force to the shoe 12, as during walking, which is distributed to the absorption means 64 through the platform 23, the dial 28, and the piston 22. The applied force causes the absorption means 64 to compress, causing the electrically conductive end of the adjustable screw 24 to approach the contacts 36,38. When enough force has been applied, the screw 24 will touch the contacts 36,38, thus energizing the signalling means. Of course, this is only one embodiment of these components and many possibilities exist which are still within the scope and spirit of the present invention. For example, shown in FIG. 4 is a second embodiment of the components contained within cavity 14.

Figure 4:
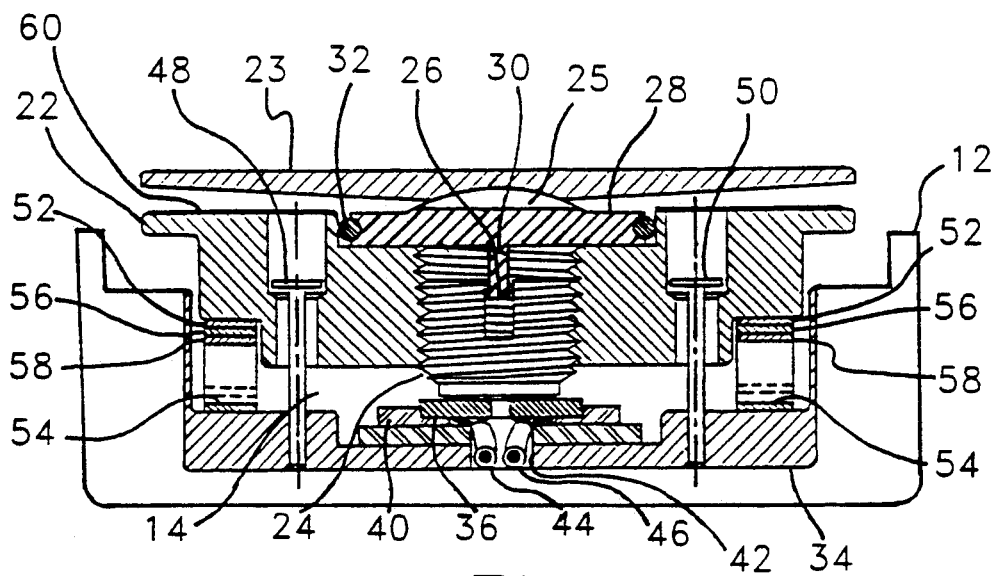
FIG. 4 is a partial cross sectional view illustrating an alternative means for determining the occurrence of a pre-selected force applied to the shoe sole.
Figure 6:
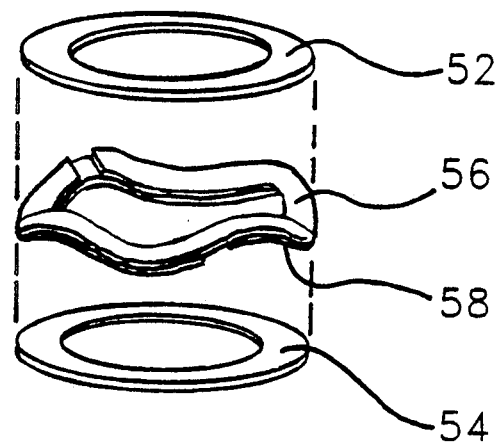
FIG. 6 is an exploded view of the components of the preferred embodiment of the force absorption system.

In the embodiment of FIG. 4, different means have been implemented for absorbing the applied force. The preferred embodiment employs wave springs 56,58 instead of an absorption means 64, as shown in FIG. 3 to absorb force. These springs 56,58 are used singly or stacked one upon another and flat shims 52,54 are placed above and below in cases where the springs 56,58 might bear upon surfaces made of material softer than the springs 56,58. The preferred embodiment is illustrated further in FIG. 6. Another difference between the embodiments of FIG. 3 and FIG. 4 is that the electrical wires 44,46 from the contacts 36,38 are now shown travelling through cavity 42, as if for connection to the signalling means. Guides 48,50 serve to keep the components from becoming separated.

Figure 5:
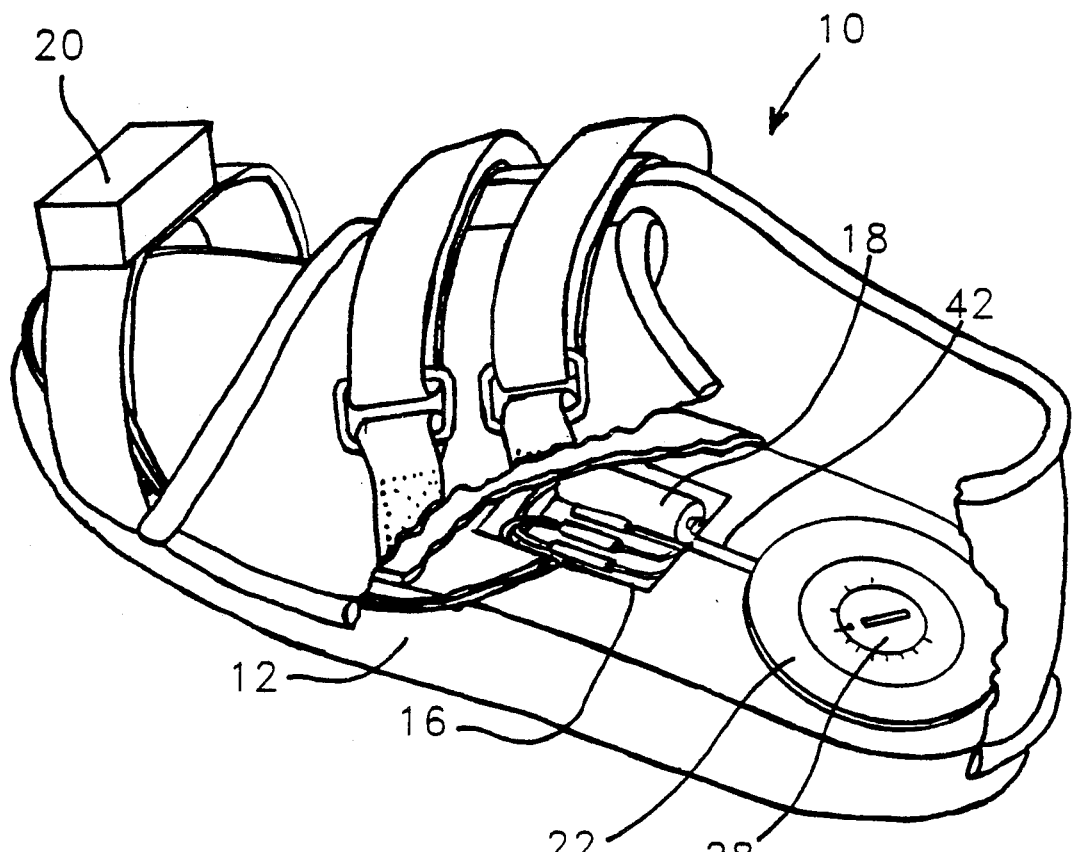
FIG. 5 illustrates, partially in section, an alternate embodiment of the present invention showing an alternate location of the signalling means.

As mentioned earlier, there are many embodiments for each component of the system 10. For example, the shoe sole 12 typically includes two basic designs: one for patients with a bare foot and another for patients wearing a cast (see FIG. 5). Of course it will be understood that other configurations are within the scope of the present invention. The shoe 10 design for a bare foot is similar to a normal shoe in shape and size, the difference being the monitoring and signalling equipment contained within. The design for a foot in a cast is bigger and has a different shape, to accommodate the cast.

The shoe sole 12 is designed such that the invention 10 can be incorporated in any shoe design the patient desires, for example, tennis shoes, sandals, boots, etc. This allows the patient to wear the device 10 every day as he would any other shoe. Although two different designs of the shoe sole 12 have currently been developed, one for a bare foot, the Other for a cast, the functions of all designs of the shoe enclosure 10 are the same. These functions include, but are not limited to, protecting the contained components from outside harm, allowing ease of use for the patient, and providing a medium through which all device 10 components can work together.

The signalling means used in the system 10 can also take several forms, for example an LED display, a shocking means, a noise means, or the aforementioned vibrational device 20 may be employed. While all of these may be effective in some cases, the vibrational means 20 is the most versatile and unobtrusive of the options.

Light emitting diodes, or LED's, can be used to display the amount of force that has been applied. A single LED can be energized when the applied force is sufficient, or a scheme of LED's could be used to display the force applied over a range of values. Problems arise in whether or not the patient will always be able to see the display. The LED's may not always be visible to the patient due to circumstances such as bright sunlight, or an excessive stomach. Further, the patient most probably will not want to walk with his face pointing down at his feet. Thus, this option is not the optimum solution.

Some type of noise means can also be employed to emit a buzz or beep when the proper amount of force has been applied. A problem arises in that the noise means may become bothersome to the patient and surrounding people in situations such as libraries or restaurants. Alternatively, the patient may not be able to hear the sound if he is on a noisy street. Thus, this is not the optimal solution.

The vibrational means 20 provides a signal directly to the shoe 10 Wearer, which is substantially unnoticeable by surrounding people. It can however, always be felt by the patient since the vibrational means 20 contacts the patient's foot. The vibrational means 20 may be located on the top of the toes or adjacent to some other part of the patient's foot. The vibrational means 20 is the option implemented in this particular embodiment, although other embodiments exist that can provide an alert which is just as effective and inconspicuous.

The shape and size of the platform 23, shown in FIG. 3 can be altered to match the contours of the patient's foot and to make a better connection to the absorption means. The platform 23, does more than just receive force from the patient's foot, it distributes the applied force evenly to the absorption means. Due to this distribution of force, comfort is provided to the patient and the absorption means performs more efficiently. The piston 22 can take many shapes and sizes depending upon the size and shape of the patient's foot, where it is placed, and the embodiments employed for the other components.

The function of the absorption means is not only to absorb the force applied to the system 10, but to do so in such a manner that the amount of applied force can be measured accurately. The embodiments of the absorption means is by no means limited to the configurations described in FIGS. 2 and 3. A variety of other methods can be utilized, for example, hydraulic means, pneumatic devices, and solid state electronic devices.

Embodiments of the absorption means employing hydraulic or pneumatic devices utilize the same basic components. A vessel, such as a piston, cylinder, or sealed bladder, absorbs the force applied by the patient's foot. These vessels would be filled with water or air, for hydraulic or pneumatic systems, respectively. A means for measuring the pressure within these vessels, such as pressure transducers or pressure gauges, could then determine the instantaneous pressure. This pressure would then be compared with the desired pressure to determine if enough force has been applied by the patient's foot. A problem with these systems is that only the instantaneous pressure can be measured, so there is no means for recording data or trends.

Solid state devices such as pressure transducers, strain gauges, or load cells can also be employed in the force absorption system. These devices are able to convert force directly to an electrical current, where the current produced is proportional to the applied force. This signal can then be used by analysis equipment to determine how much force is being applied, when it was applied, and any other desired data. Microprocessors and other solid state devices can easily be incorporated into this embodiment to provide memory and processing functions as desired by the physician.

The solid state force absorption means without question would provide the most comprehensive medical data. Not only could it measure the amount of force applied very accurately, if used in conjunction with a microprocessor it could store the results for examination by a physician. The doctor would be able to determine the highs, lows, and any necessary trends from the data. No other method can provide this level of service. Unfortunately, the electronic method is difficult and expensive to implement, so for the initial design, a spring mechanism will be used and discussed.

The characteristics of the springs 56, 58 in FIG. 4 can be modified to accommodate the individual absorption requirements of each patient. For example, due to differences in weight, the severity of the injury, and how far along in recovery the patient has come, some patients could need an absorption range of 10 to 100 lbs, while others might require a range of 60 to 150 lbs. By modifying the number of or the characteristics of the springs 56, 58, such as compressibility, durability, etc., the device 10 can be made to cover any range of values a patient may require. The characteristics can be modified by altering the production process and the materials used to fabricate the springs 56,58. The preferred means of using stacked springs 56,58 permits the use of additional springs to accommodate higher force ranges or a single spring for lower force ranges.

Determining the amount of force applied to the patient's leg is relatively easy when the spring means 56, 58 is implemented. The force absorbed by a spring is directly proportional to the spring characteristics and the amount of compression the spring undergoes. Since the spring characteristics are controlled and known, by measuring the degree of compression the spring undergoes, the amount of force applied to the spring 56 can be determined.

The force selection screw 24 controls when the patient alert system is activated. The physician can adjust the amount of force he wishes the patient to apply by changing the initial height, relative to the piston 22, of the adjustment screw 24. As described earlier, when force is applied to the system 10, the force absorbing means compresses, allowing the electrically conductive end of the screw 24 to approach the contacts 36,38. If the screw 24 is close to the contacts, 36,38, little force will be required to energize the alert system, but if the screw 24 is set high above the contacts, 36,38, then a considerable amount of force may be needed. Adjustments can be made via the dial 28 which is restrained by the retainer 32, both of which are located on top of the screw 26, as shown in FIG. 4.

A force sensitive shoe has been designed to aid in the rehabilitation of injured legs. A piston distributes the force applied by the patients foot to force absorbing springs. The springs compress due to the force, displacing the piston and an electrically conductive screw downward. If enough force is applied, the screw will touch two contacts which will cause a vibration in the shoe. This vibration will inform the patient that enough force has been applied to the leg. The amount of force that must be applied to achieve a vibration can be altered by a physician by lowering or raising the adjustment screw.

In the foregoing detailed description, a medical device has been shown and described which will greatly aid the recuperation of some patients. Those with leg injuries will no longer have to guess if they are placing 50% or 60% of their weight on their leg because the device will automatically tell them. The present invention will not only accelerate the healing process, it will prevent re-injuries.

While a preferred embodiment has been shown and described, it will be understood that it is not intended to limit the disclosure, but rather it is intended to cover all modifications and alternate methods falling within the spirit and the scope of the invention as defined in the appended claims.

Having thus described the aforementioned invention, we claim:

1. A portable force monitoring device for regulating a selected force applied to a leg of a wearer, said portable force monitoring device comprising:
   a body member to support at least a portion of a foot of the wearer, said body member having a sole member defining an upper surface for support of the foot of a lower surface to contact a support surface, said upper surface provided with a cavity in a heel portion of said sole member, said cavity having a bottom wall;
   covering member to close an upper opening into said cavity;
   a force sensing unit within said cavity beneath said covering member, said force sensing unit having
   a) a switch means mounted proximate said bottom wall of said cavity,
   b) a piston member mounted within said cavity,
   c) an adjustment screw threadably engaged with said piston member, said adjustment screw having a first end portion, and a distal end portion directed toward said switch means, whereby rotation of said adjustment screw positions said distal end portion a selected distance from said switch means to select said selected force,
   d) a force concentrator having an upper surface substantially in contact with said covering member and a lower surface in contact with said fist end portion of said adjustment screw whereby force applied by a heel of the wearer's foot is concentrated by said force concentrator upon said first end of said adjustment screw, and
   e) a force absorption unit surrounding said piston member to bias said piston member containing said adjustment screw away from said switch means; and said first end of said adjustment screw is provided with a rotatable dial member for rotation of said adjustment screw, said dial member having an exposed central pivot surface, and wherein said force concentrator is a platform member extending substantially across said heel portion of said sole member to receive force applied to said force sensing unit by the foot of the wearer, said platform member having an upper surface substantially in contact with an undersurface of said covering member and a lower surface pivotally contacting said pivot surface of said dial member whereby uneven force applied by the wearer is concentrated upon said first end of said adjustment screw; and
   a signal producing circuit connected to said switch means to provide the wearer with a signal when said selected force is reached or exceeded to thereby regulate said force.

2. The device of claim 1 wherein said force absorption unit comprises at least one wave spring surrounding said piston member.

3. The device of claim 1 wherein said force absorption unit comprises a pair of stacked wave springs sandwiched between a pair of flat shim washers.

4. The device of claim 1 wherein said switch means comprises:
   a pair of conductive contacts mounted proximate said bottom wall of said cavity; and
   a conductive layer applied to said distal end of said adjustment screw.

5. The device of claim 1 wherein said signal producing circuit comprises:
   a source of electrical power;
   a vibrational motor in contact with an under surface of said covering member to produce vibrations against a bottom of the wearer's foot; and
   electrical conductors connecting said switch means with said source of electrical power and said vibrational motor.

6. The device of claim 5 wherein said source of electrical power and said vibrational motor are positioned within a second cavity provided within said upper surface of said sole member.

7. The device of claim 1 wherein said adjustment screw is provided with a transverse slot in said first end, and wherein said dial member is provided with a tang to be received in said slot whereby rotation of said dial member causes rotation of said adjustment screw.

8. The device of claim 1 wherein a base member is positioned within said cavity of said sole portion, said base member being provided with a cavity, and wherein said force sensing unit is positioned within said cavity of said base member.

9. The device of claim 1 wherein said body member is a shoe body to at least partially embrace the foot the wearer.

10. A portable force monitoring device for regulating a selected force applied to a leg of a wearer, said portable force monitoring device comprising:
   a body member to embrace at least a portion of a foot of the wearer, said body member having a sole member defining an upper surface for support of the foot and a lower surface to contact a support surface, said upper surface provided with a cavity in a heel portion of said sole member, said cavity having a bottom wall;
   a covering member to close an upper opening into said cavity;
   a force sensing unit within said cavity beneath said covering member, said force sensing unit having a) a switch means mounted proximate said bottom wall of said cavity, b) a piston member mounted within said cavity, c) an adjustment screw threadably engaged with said piston member, said adjustment screw having a first end portion, and a distal end portion directed toward said switch means, whereby rotation of said adjustment screw positions said distal end portion a selected distance from said switch means to select said selected force, d) a rotatable dial member carried by said first end of said adjustment screw for rotation of said adjustment screw, said dial member having an exposed central pivot surface, e) a platform member extending substantially across said heel portion of said sole member and having an upper surface substantially in contact with said covering member and a lower surface in pivotal contact with said pivot surface of said dial member whereby uneven force applied by a heel of the wearer's foot is concentrated by said platform member upon said dial member and thus said first end of said adjustment screw, and f) a pair of stacked wave springs surrounding said piston member to bias said piston member containing said adjustment screw away from said switch means; and a signal producing circuit connected to said switch means to provide the wearer with a signal when said selected force is reached or exceeded to thereby regulate said force.

11. The device of claim 10 wherein said signal producing circuit comprises:

a source of electrical power;

a vibrational motor in contact with an under surface of said covering member to produce vibrations against a bottom of the wearer's foot; and electrical conductors connecting said switch means with said source of electrical power and said vibrational motor.

12. The device of claim 11 wherein said source of electrical power and said vibrational motor are positioned within a second cavity provided within said upper surface of said sole member.

13. The device of claim 10 wherein said adjustment screw is provided with a transverse slot in said first end, and wherein said dial member is provided with a tang to be received in said slot whereby rotation of said dial member causes rotation of said adjustment screw.

14. A portable force monitoring device for regulating a selected force applied to a leg of a wearer, said portable force monitoring device comprising:

a body member to embrace at least a portion of a foot of the wearer, said body member having a sole member defining an upper surface for support of the foot and a lower surface to contact a support surface, said upper surface provided with first and second cavities in a heel portion of said sole member, said cavities each having a bottom wall;

a covering member to close an upper opening into said cavities;

a force sensing unit within said first cavity beneath said covering member, said force sensing unit having a) a switch means mounted proximate said bottom wall of said cavity, b) a piston member mounted within the cavity, c) an adjustment screw threadably engaged with said piston member, said adjustment screw having a first end portion provided with a transverse slot, and a distal end portion directed toward said switch means, d) a rotatable dial member having a tang engaged with said slot of said first end of said adjustment screw whereby rotation of said dial member rotates said adjustment screw to position said distal end portion a selected distance from said switch means to select said selected force, said dial member having an exposed central pivot surface, e) a platform member extending substantially across said heel portion of said sole member and having an upper surface substantially in contact with said covering member and a lower surface in pivotal contact with said pivot surface of said dial member whereby uneven force applied by a heel of the wearer's foot is concentrated by said platform member upon said dial member and thus said first end of said adjustment screw, and f) a pair of stacked wave springs surrounding said piston member to bias said piston member containing said adjustment screw away from said switch means; and a signal producing circuit mounted in said second cavity and connected to said switch means to provide the wearer with a signal when said selected force is reached or exceeded to thereby regulate said force.

15. The device of claim 14 wherein said signal producing circuit comprises:

a source of electrical power;

a vibrational motor in contact with an under surface of said covering member to produce vibrations against a bottom of the wearer's foot; and electrical conductors connecting said switch means with said source of electrical power and said vibrational motor.

16. The device of claim 14 wherein said switch means comprises:

a pair of conductive contacts mounted proximate said bottom wall of said first cavity; and a conductive layer applied to said distal end of said adjustment screw.

* * * * *

UNITED STATES PATENT AND TRADEMARK OFFICE
CERTIFICATE OF CORRECTION

PATENT NO.    : 5,269,081
DATED         : December 14, 1993
INVENTOR(S)   : Frank B. Gray and John L. Parris (as corrected below)

It is certified that error appears in the above-identified patent and that said Letters Patent is hereby corrected as shown below:

On the title page, item [76]:

Inventors:    Frank B. Gray, 5104 Lyons View
                       Pike, Knoxville, Tenn. 37919,
                       John L. Parris, 314 Kennon Road,
                       Knoxville, Tenn. 37909

Signed and Sealed this

Thirtieth Day of May, 1995

Attest:

BRUCE LEHMAN

Attesting Officer      Commissioner of Patents and Trademarks